United States Patent [19]

Setsuda et al.

[11] 4,271,318

[45] Jun. 2, 1981

[54] PROCESS FOR PREPARING AMINO SCHIFF BASE OR CORRESPONDING DIAMINO KETONE

[75] Inventors: Tsutomu Setsuda, Ogaki; Hideyuki Aizawa, Aichi; Takeshi Kimura, Nagoya, all of Japan

[73] Assignee: Toray Industries, Inc., Tokyo, Japan

[21] Appl. No.: 79,830

[22] Filed: Sep. 28, 1979

[51] Int. Cl.³ .................. C07C 85/12; C07C 85/147; C07C 85/153; C07C 85/20

[52] U.S. Cl. .................. 564/468; 260/239 BE; 260/326.85; 546/246; 562/553; 564/487; 564/502

[58] Field of Search ......... 260/584 A, 583 P, 239 BE, 260/326.85; 562/553; 546/246

[56] References Cited

U.S. PATENT DOCUMENTS

| | | | |
|---|---|---|---|
| 2,327,119 | 8/1943 | Martin | 562/553 |
| 2,870,201 | 1/1959 | Pollack | 562/553 X |
| 3,412,156 | 11/1968 | Ueda et al. | 260/584 A X |
| 3,655,748 | 4/1972 | Tandara | 562/553 |
| 3,663,643 | 5/1972 | Hall | 585/612 X |
| 3,974,215 | 8/1976 | Goulay | 562/553 X |

FOREIGN PATENT DOCUMENTS

| | | | |
|---|---|---|---|
| 1131697 | 6/1962 | Fed. Rep. of Germany | 564/487 |
| 1493897 | 4/1969 | Fed. Rep. of Germany | 562/553 |
| 1268848 | 6/1961 | France | 564/487 |
| 2255290 | 7/1975 | France | 564/502 |
| 3716015 | 10/1960 | Japan | 564/502 |
| 790503 | 2/1958 | United Kingdom | 562/553 |

OTHER PUBLICATIONS

Wagner & Zook, "Synthetic Organic Chemistry," p. 416 (1963).

Primary Examiner—John Doll
Attorney, Agent, or Firm—Miller & Prestia

[57] ABSTRACT

An $\omega$-lactam having 4–12 carbon atoms, an oligomer thereof or a ring-opened polymer or an $\omega$-amino carboxylic acid corresponding thereto, is heated in the presence of water and a metallic carbonate compound to obtain a metallic salt of $\omega$-amino carboxylic acid. Barium, calcium and lithium are the preferred metals. The resulting metal salt is converted to an amino Schiff base which may be used as a starting material for preparing an $\alpha,\omega$-diamino alkane which may or may not include an amino group as a side chain. This further produces a metallic carbonate compound. The metallic carbonate is returned and used again as a reagent for forming the metal salt of the $\omega$-amino carboxylic acid to create a closed system.

11 Claims, 1 Drawing Figure

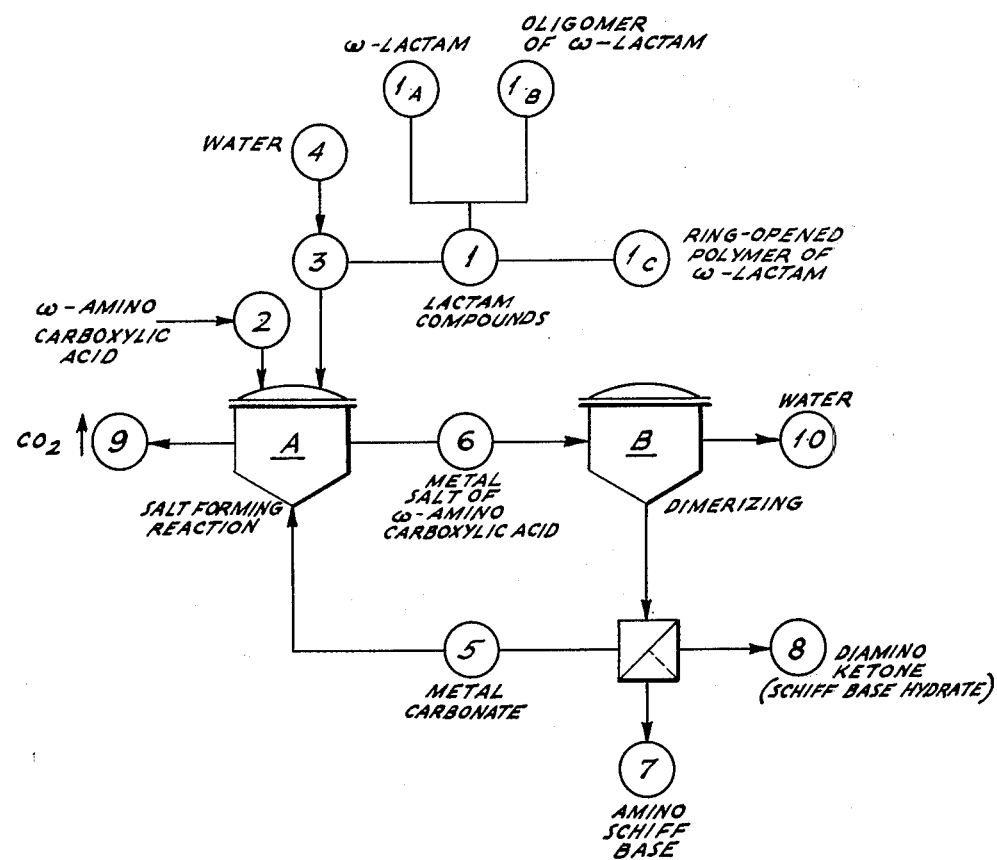

PROCESS FOR PREPARING AMINO SCHIFF BASE OR CORRESPONDING DIAMINO KETONE

BACKGROUND OF THE INVENTION (1) Field of the Invention

The present invention relates to a process for preparing an amino Schiff base or a diamino ketone corresponding thereto.

(2) Description of the Art

It is known that an $\omega$-lactam having 4–12 carbon atoms, a linear or cyclic oligomer thereof or a ring-opened polymer thereof may be converted to an $\omega$-amino carboxylic acid, which may be used as a starting material for preparing a dimer having the general formula

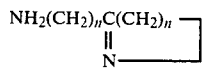

which is known as an amino Schiff base.

Japanese Published Unexamined patent application No. 137974/1975 is a relevant disclosure of such base. The amino Schiff base may be converted to an $\alpha,\omega$-diamino alkane which may or may not include an amino group as a side chain. This is indicated, for example, by British Pat. No. 995,482 and U.S. Pat. No. 3,412,156. In order to obtain such an amino Schiff base, an alkali metal hydroxide, alkali earth metal oxide or alkali earth metal hydroxide may be reacted with an $\omega$-lactam. This has been proposed in Japanese Published Examined patent application No. 7432/1973, in British Pat. No. 922,275 and in West German Pat. No. 1,131,697.

According to this process, an alkali metal carbonate or an alkali earth metal carbonate is stoichiometrically produced as a by-product. Unless this carbonate is converted to a hydroxide and is reused, the problem remains that the metal hydroxide is consumed in an amount corresponding to the amount of the amino Schiff base produced.

It is suggested in Japanese Published Examined patent application No. 7432/1973 that a so-called recovery process may be provided for converting a metal carbonate to a metal hydroxide and reusing the same. However, if such a recovery process is resorted to for obtaining an amino Schiff base from an $\omega$-lactam, etc., additional costs would be required for recovering alkali metal. Therefore, processes for preparing amino Schiff bases, accompanied by recovery processes, are still in need of drastic improvement.

BRIEF SUMMARY OF THE INVENTION

An important object of the present invention is to provide a series of steps which comprise a salt-forming step for producing a metal salt of an $\omega$-amino carboxylic acid from a lactam compound such as an $\omega$-lactam having 4–12 carbon atoms, its oligomer or a ring-opened polymer thereof, or an $\omega$-amino carboxylic acid having 4–12 carbon atoms, and a dimerizing step for forming an amino Schiff base by decarboxylating and dimerizing said metal salt of said $\omega$-amino carboxylic acid.

Another object of this invention is to overcome the difficulties heretofore encountered in the art by providing a novel salt-forming step which is capable of using the by-product produced in the aforementioned dimerizing step.

The foregoing and other objects are effectively achieved by providing a process which comprises:

(A) forming a metal salt of an $\omega$-amino carboxylic acid by heating a starting material comprising (a) an $\omega$-lactam having 4–12 carbon atoms or (b) an oligomer thereof, or (c) a ring-opened polymer thereof, or (d) an $\omega$-amino carboxylic acid with water and a carbonate of a metal selected from the group consisting of lithium, calcium and barium, in a heat reaction container heated at a temperature of about 60°–350° C., and discharging the carbon dioxide produced by the reaction;

(B) dimerizing the $\omega$-amino carboxylic acid by heating the resulting metal salt at a temperature of about 250°–550° C., thereby producing an amino Schiff base and/or a corresponding diamino ketone or hydrated amino Schiff base, and also producing a carbonate of a metal selected from the group consisting of lithium, calcium and barium, and (C) recycling the metal carbonate compound obtained from the dimerizing step by returning it to the salt-forming step (A) and re-using it as a starting material.

BRIEF DESCRIPTION OF THE DRAWING

The drawing is a schematic flow diagram illustrative of the process of the present invention.

DETAILED DESCRIPTION OF THE INVENTION

As shown in the drawing, when water is utilized in the reaction container (A), the feed materials comprise at least one lactam material (3) selected from the group consisting of $\omega$-lactam (1A), an oligomer thereof (1B) and a ring-opened polymer thereof (1C), (hereinafter referred to as lactam compounds (1)), or an $\omega$-amino carboxylic acid (2), water (4) and a metal carbonate (5), all of which are supplied to the heat reaction container (A).

As an example, $\omega$-lactam (1A), water (4) and a metal carbonate such as lithium carbonate (5) undergo a salt formation reaction as follows:

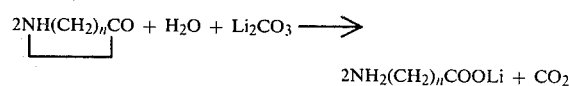

Accordingly, water and lithium carbonate in amounts of at least 0.5 mol per mol of $\omega$-lactam (1A) may be supplied. However, lithium carbonate may be used in an amount up to about 5.0 mols and water in an amount up to about 500 mols, both base on one mol of $\omega$-lactam (1A).

On the other hand, the reaction of the $\omega$-amino carboxylic acid (2) with the metal carbonate (5) theoretically proceeds in the absence of water. However, unless water is present, a major part of the $\omega$-amino carboxylic acid cyclizes to produce a lactam. Therefore, water is used in that reaction to prevent such reaction. It is possible to use a water-soluble solvent such as a lower alcohol, in addition to water, in order to increase the solubility of the lactam compounds (1).

Upon heating the starting materials in the heat reaction container (A), a metal salt of an $\omega$-amino carboxylic acid is produced, as indicated by the reaction set forth above.

Heating is normally carried out at a temperature of about 60°–350° C. However in commercial production, it is preferable to carry out heating at a temperature of about 150°–300° C. under increased pressure.

In the present invention, as will be apparent from the aforementioned reaction formula, carbon dioxide is produced as the reaction proceeds. It is necessary to discharge this carbon dioxide (9) from the heat reaction container (A), either during or after the completion of the reaction. This is carried out in the usual way.

In order to promote the reaction, it is possible to supply a gas such as $N_2$, He or air to the heat reaction container (A), or to effect heating of the starting materials in the atmosphere of such a gas stream, or to effect heating of the materials while continuously supplying superheated steam to the heat reaction container (A) and to release the steam from the heat reaction container (A).

In any event, an aqueous solution (6) of a metal salt of an $\omega$-amino carboxylic acid is obtained. When the solvent is removed from this aqueous solution in the usual way, crystals of the metal salt of the $\omega$-amino carboxylic acid are obtained.

The resulting metal salt of the $\omega$-amino carboxylic acid, or the aqueous solution reaction mixture thereof, is used per se as the feed material for the subsequent dimerizing step. In this dimerizing step, the metal salt of the $\omega$-amino carboxylic acid (6) is supplied to a heat reaction container (B), where the dimerizing reaction takes place. As an example, lithium $\omega$-amino carboxylate (6) reacts to produce lithium carbonate (5) and water (10), besides amino Schiff base (7) or diamino ketone (8) which is a ring-opened hydrate of said base.

A typical reaction in container (B) is as follows:

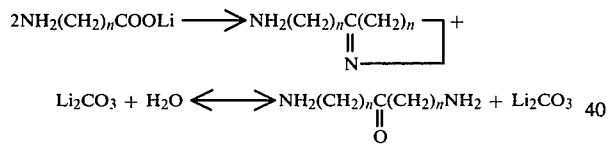

where n is an integer from 3 to 11.

The temperature in the heat reaction container (B) is about 250°–550° C. and more preferably about 300°–400° C. The higher the heat temperature, the greater the reaction rate. However, at higher temperatures, the yield of amino Schiff base (7) or diamino ketone (8) is likely to be reduced.

The amino Schiff base (7) and the diamino ketone (8) produced in the heat reaction container (B) are distilled off in order and may be collected as distillates. On the other hand, the metal carbonate compound (5) is readily obtained as granules by washing the residue in the container (B) with a solvent, preferably water, after the distillates have been taken off.

The metal carbonate compound (5) which is obtained at good yield may be supplied again to the aforementioned heat reaction container (A) and reused as a starting material for the salt-forming step.

Accordingly, the metal carbonate compound recycles between the salt-forming step and the dimerizing step. By such circulation and reuse of the metal carbonate compound, a closed system is established between the salt-forming step and the dimerizing step.

Examples of $\omega$-lactams having 4–12 carbon atoms as used in the present invention include $\alpha$-pyrrolidone, $\alpha$-piperidone, $\epsilon$-caprolactam, $\zeta$-heptanolactam, $\eta$-capryllactam, and $\omega$-laurolactam. In the practice of the present invention, various linear or cyclic oligomers of these lactams or ring-opened polymers of these lactams may be utilized. Also, an $\omega$-amino carboxylic acid having 4–12 carbon atoms may be used.

However, lactam compounds, such as $\omega$-lactam, oligomers thereof, and ring-opened polymers thereof, having 4–6 carbon atoms, are preferably used in the present invention. $\epsilon$-caprolactam, its oligomer or polycaproamide (nylon-6), which is a ring-opened polymer of $\epsilon$-caprolactam, are more preferably used, since they are readily and inexpensively available.

On the other hand, carbonates of metals selected from the group consisting of lithium, calcium and barium as decomposition agents for the lactam compounds and as salt-forming agents for the $\omega$-amino carboxylic acid. Lithium carbonate, calcium carbonate or barium carbonate are preferably used as the metal carbonate in the present invention. However, lithium carbonate and calcium carbonate are more preferably used, and lithium carbonate is most preferable.

The process of the present invention may be put into effect either continuously or batchwise. If batchwise, the reaction of the salt-forming step and the reaction of the dimerizing step may be conducted in the same reaction apparatus.

Hereinbelow, the present invention will be explained in detail by reference to examples, in which the mol numbers of polymer and oligomer are based on the mol number of the amide group as a standard. The specific examples are intended to serve as illustrations of specific ways in which the invention may be carried into effect, but are not intended to define or to limit the scope of the invention, which is defined in the appended claims.

EXAMPLE 1

Step 1. Preparation of $\epsilon$-aminocaproic acid lithium salt

A one liter autoclave equipped with a water cooling relux condenser (Reactor A) was charged with 45.3 g (0.4 mol) of $\epsilon$-caprolactam (Lc), 14.8 g (0.2 mol) of lithium carbonate and 360 ml of water. The reactor was flushed with nitrogen. The contents of the reactor were heated and refluxed at a temperature of 200° C. under a nitrogen stream. The flow rate of nitrogen was 50 ml/min. Reflux continued for 6 hours while maintaining a pressure of 10–11 kg/cm$^2$.

During the reaction period, an exhaust gas containing carbon dioxide by-products was introduced into an aqueous solution of caustic soda, and the absorbed carbon dioxide was determined by acidometry at regular time intervals to follow the extent of the salt-formation reaction.

The amount of carbon dioxide was 0.198 mol (21.0 g as sodium carbonate) for 6 hours and the conversion of Lc to $\epsilon$-aminocaproic acid lithium salt (ACA Li) was 99.2 mol %.

After completion of the reaction, excess water was released as steam and the contents of the autoclave were concentrated to about 100 ml.

Step 2. Preparation of amino Schiff base and Recovery of $Li_2CO_3$

The concentrated liquid was transfered to a 200 ml dry-distilling flask (Reactor B) and heated at 100°–150° C. under stirring and then heated at a temperature of about 340°–360° C. under a nitrogen stream for 2.5 hours. 37.6 g of a light yellow distillate were obtained. The distillate contained 33.2 g of amino Schiff base (ASB:7-(5'-aminopentyl)-3,4,5,6-tetrahydro-2H-azepine) and 2.76 g of Lc. The yield of ASB on the base of reacted Lc was 96.8.

On the other hand, 50 ml of water were added into the solid residue in the reactor and the contents of reactor were refluxed for 1 hour with stirring. After cooling to room temperature, the solid residue was recovered by filtration. 14.3 g of a grayish white powder of $Li_2CO_3$ were obtained (purity: 99.3%) and the recovery of $Li_2CO_3$ on the basis of $Li_2CO_3$ fed to the salt-formation was 96%. When the normal operational loss was taken into account, the recovery of $Li_2CO_3$ could be considered quantitative.

Step 3. Reuse of $Li_2CO_3$ Recovered

Using $Li_2CO_3$ recovered from Step 2, the reactions (Steps 1 and 2) were carried out by the methods previously mentioned above.

Into the autoclave (Reactor A) 14.2 g $Li_2CO_3$ recovered from Step 2, 0.6 g. of fresh $Li_2CO_3$ and 45.3 g of Lc were introduced together with 360 ml of water. The reaction result showed 98.3 mol % conversion of Lc to ACA Li.

Then, the ACA Li was dry distilled under similar conditions as mentioned above (Step 2). The distillate contained 32.8 g of ASB and 2.76 g of Lc. The yield of ASB on the basis of reacted Lc was 95.7%. The amount of lithium carbonate recovered was 14.3 g and the recovery of $Li_2CO_3$ was 97%.

EXAMPLE 2

Polycapramide (nylon-6), $\eta_\gamma = 3.40$) was used in one reaction, and oligocapramide was used in a separate reaction. The oligocapramide was a white powder consisting mainly of the cyclic dimer and the cyclic trimer. They were used in amounts of 45.3 g (0.4 mol), respectively. 14.8 g (0.2 mol) of lithium carbonate and 360 ml of water were charged into the separate autoclaves A and A', corresponding to the salt-formation reactor of Example 1. As in Example 1, the temperature of each was elevated to 250° C., at which temperature and in a $N_2$ stream, the contents of the two autoclaves were separately reacted. The ratios of lithium ϵ-amino caproate produced, as calculated from the amounts of carbon dioxide produced, are shown in Table 1.

After completion of the reactions, the reaction liquid in the polycapramide autoclave was evaporated, dried and solidified to obtain 54.7 g (purity: 98.5%) of white crystals of lithium ϵ-amino caproate. On the other hand, the reaction liquid in the oligocapramide autoclave A' was concentrated to 100 ml.

The resulting white crystals were charged into the same heat apparatus as in Example 1 (dimerizing container B) and melted at a temperature of 235°–240° C.

Thereafter, the concentrated liquid was charged in the same heat apparatus as in Example 1 (container B'). Both of the reactors B and B' were heated by the same procedure as in Example 1 to obtain 38.5 g and 37.1 g of light yellow liquids, respectively.

Analyses of the distillate liquids, using the method of Example 1, are shown in Table 1.

The residues in these two reactors B and B' were treated the same as in Example 1 to recover lithium carbonate.

EXAMPLE 3

A one liter flat bottom flask equipped with a reflux device was charged with starting materials comprising 52.5 g (0.4 mol) of ϵ-amino caproic acid, 16.3 g (0.22 mol) of lithium carbonate and 500 ml of water. While the starting material was heated and refluxed for about 20 hours in an $N_2$ atmosphere, the carbon dioxide produced was absorbed in an aqueous solution of caustic soda and quantitatively analyzed by acidometry. The amount of carbon dioxide produced was 20.1 g (0.19 mol) on the basis of sodium carbonate. This result means that 95.0% of the ϵ-amino caproic acid starting material was converted to lithium ϵ-amino caproate.

After completion of the salt-forming reaction, the reaction product mixture was concentrated to about 100 ml, transferred to another reactor and heated and distilled in the same manner as in Example 1 to obtain 36.9 g of a light yellow distillate (reaction temperature: 340°–360° C., time required for distillation: 2.5 hours).

As a result of analyzing this distillate by gas chromatography it was found that 86.4% and 7.6% of ϵ-amino caproic acid were

TABLE 1

| | | Percentage of lithium ϵ-amino caproate produced | Conditions for synthesizing ASB | | Reaction Results | | | |
|---|---|---|---|---|---|---|---|---|
| Example | Material | | Temperature (°C.) | Time (hr) | Percentage of ASB produced | Percentage of Lc produced | Production ratio of ASB[a] (%) | Recovery of lithium carbonate (%) |
| 2-1 | Polycapramide | 98.3 | 310–330 | 6 | 90.5 | 5.3 | 95.6 | 95 |
| 2-2 | Oligocapramide | 97 | 370–390 | 1 | 87.3 | 4.7 | 91.6 | 96 |

Note:
[a]Production ratio of ASB is based on reacted lactam.

converted into ASB and ϵ-caprolactam. The yield of ASB was 93.6%. The yields of lithium carbonate were 15.8 g, and 97% of the lithium carbonate used as the starting material was recovered. All the resulting lithium carbonate was used again for preparing lithium ϵ-amino caproate.

EXAMPLE 4

Using 45.3 g (0.4 mol) of ϵ-caprolactam as the starting material and $CaCO_3$ or $BaCO_3$, the effect of the present invention under conditions corresponding to Example 1 was observed.

The conditions for synthesizing the metal salts of ϵ-amino caproic acid and the produced ratios (mol %) of said salts calculated from the produced amount of carbon dioxide are shown in Table 2. Separately, the metal salts of ϵ-amino caproic acid were isolated and their melting points were measured by differential thermal analysis. The results are shown in Table 2.

TABLE 2

| Example No. | Reaction conditions | | | | Metal ε-aminocaproate | |
|---|---|---|---|---|---|---|
| | metal carbonate[a] | Water/ lactam weight ratio | Temp (°C.) | Time (hr) | Produced ratio (%) | Melting point (°C.) |
| 4-1 | CaCO₃ | 8.0 | 250 | 8 | 45.0 | 166 |
| 4-2 | BaCO₃ | 8.0 | 250 | 8 | 51.3 | 146 |

[a]Amount of metal carbonate charged: 0.2 mol

The produced liquids obtained by the reactions shown in Table 2 were continuously concentrated and the residues were heated and dry distilled in an N₂ stream to obtain ASB. The reaction conditions and reaction results are tabulated in Table 3.

TABLE 3

| Ex. No. | Conditions for synthesizing ASB | | Reaction Results | | | |
|---|---|---|---|---|---|---|
| | Temp. (°C.) | Distillation time (hr) | Percentage of ASB produced | Percentage of lactam produced | Yield of ASB[a] (%) | ratio of carbonate (%) |
| 4-1 | 310–320 | 6.0 | 35.1 | 52.9 | 74.4 | 97 |
| 4-2 | 310–320 | 6.0 | 38.5 | 54.4 | 84.4 | 98 |

[a]Produced ratio of ASB based on reacted lactam.

EXAMPLE 5

Tests were conducted using lithium carbonate as the metal salt and using the same apparatus and reaction method as in Example 1, but varying the kind of lactam.

The conditions for synthesizing lithium ω-aminoalkane carboxylate and the ratios (mol %) of lithium ω-aminoalkane carboxylate produced, calculated from the amounts of carbon dioxide produced, are reported in Table 4. Separately, the melting points (by differential thermal anaylsis) of the isolated lithium ω-aminoalkane carboxylates are also shown in Table 4.

TABLE 4

| Ex. No. | Reaction conditions[a] | | | Lithium ξ-aminoalkane carboxylate H₂N(CH₂)ₙCO₂Li | |
|---|---|---|---|---|---|
| | Lactam | Temp. (°C.) | Time (hr) | Percentage Produced | Melting point (°C.) |
| 5-1 | γ-amino butyric acid | 200 | 3.0 | 96.3 | 176 (n = 3) |
| 5-2 | α-pyrrolidone | 250 | 8.0 | 61.1 | 176 (n = 3) |
| 5-3 | δ-amino valerianic acid | 200 | 3.0 | 95.6 | 208 (n = 4) |
| 5-4 | α-piperidone | 250 | 8.0 | 71.7 | 208 (n = 4) |

[a]The following common conditions were met:
Amount of material charged: 0.4 mol, lithium carbonate: 0.22 mol and water: 360 ml.

The liquids obtained by the reactions shown in Table 4, above, were continuously concentrated. Thereafter, the residues were heated at 310°–330° C. and dry distilled (distillation time: 4 hours) to obtain ASB's corresponding to the lactams. The reaction results are summarized in Table 5.

TABLE 5

| Example No. | Produced ASB n[a] | Percentage of ASB produced | Recovery ratio of lactam (%) | Yield of ASB[b] (%) | Recovery ratio of lithium carbonate (%) |
|---|---|---|---|---|---|
| 5-1 | n = 3 | 85.8 | 10.3 | 95.7 | 96 |
| 5-2 | n = 3 | 50.1 | 39.8 | 83.2 | 95 |
| 5-3 | n = 4 | 81.7 | 12.7 | 93.6 | 96 |
| 5-4 | n = 4 | 57.4 | 35.2 | 88.6 | 97 |

[a]$H_2N(CH_2)_n\overset{\overset{N}{\|}}{C}(CH_2)_n$

[b]Ratio of ASB produced based on reacted lactam.

EXAMPLE 6

The same salt-forming reaction as Example 1 was carried out, using 45.3 g (0.4 mol) of ε-caprolactam, various amounts of lithium carbonate and water, and produced at various temperatures as shown in Table 6 which follows. The reactions results are also shown in Table 6.

TABLE 6

| Ex. No. | Reaction conditions | | | | Production ratio of ACA Li[a] |
|---|---|---|---|---|---|
| | Li₂CO₃/lactam molar ratio | Water/lactam weight ratio | Temp. (°C.) | Time (hr) | |
| 6-1 | 0.3 | 5.0 | 200 | 2 | 60.2 |
| 6-2 | 3.0 | 5.0 | 180 | 9 | 92.0 |
| 6-3 | 0.5 | 8.0 | 140 | 10 | 51.3 |
| 6-4 | 0.5 | 3.0 | 200 | 8 | 88.6 |

[a]The production ratios (mol %) of ACA Li, calculated from the amount of carbon dioxide produced, are shown in table 6.

The resulting reaction mixtures were concentrated and the concentrated mixtures were heated and distilled under atmospheres of N₂. ASB was obtained as a distillate. The reaction conditions and results are shown in Table 7.

TABLE 7

| Ex. No. | Reaction Conditions | | Reaction Results | | | |
|---|---|---|---|---|---|---|
| | Temperature (°C.) | Distillation time (hr) | Percentage of ASB produced | Recovery ratio of lactam (%) | Production ratio of ASB[a] (%) | Recovery ratio of lithium carbonate (%) |
| 6-1 | 310–30 | 5.0 | 53.3 | 38.4 | 86.5 | 93 |
| 6-2 | 310–30 | 5.0 | 83.1 | 7.2 | 89.5 | 99 |
| 6-3 | 340–50 | 3.5 | 47.2 | 46.7 | 88.6 | 95 |
| 6-4 | 340–50 | 4.0 | 76.6 | 10.3 | 85.4 | 96 |

[a]Production ratio of ASB based on reacted lactam.

EXAMPLE 7

11.3 g (0.1 mol) of ε-caprolactam, 4.1 g (0.055 mol) of lithium carbonate and 68 ml of water were charged into a 0.3 liter autoclave with a gas outlet equipped with a water cooling pipe and a gas inlet.

The air inside the autoclave was replaced by nitrogen gas, and a pressure adjusting valve was closed at the same time to start stirring. The autoclave was heated to a predetermined temperature by an electric heater. About 50 minutes after heating was started, the temperature reached 200° C. and the gauge pressure of the autoclave became 10–11 kg/cm².

At this point, the pressure adjusting valve of the gas inlet was adjusted so as to equalize the nitrogen pressure to the pressure inside the autoclave while nitrogen gas was being supplied at a rate of 50 ml/min and the gas was being continuously exhausted via a pressure reducer in the gas inlet.

At 200° C. the content of the autoclave was heated and refluxed for 6 hours. In the meantime, the carbon dioxide produced was absorbed in an aqueous solution of caustic soda.

After completion of the reaction, the reaction mixture in the autoclave was cooled to room temperature. Thereafter, it was transferred to a 200 ml flask and concentrated to about 40 ml under reduced pressure. Continuously, an excess amount of lithium carbonate was filtered out to obtain an aqueous solution containing lithium ε-amino caproate. Using benzene, the unreacted ε-caprolactam was extracted and removed. Thereafter, the amount of lithium ε-amino caproate in the aqueous solution was quantitatively analyzed in the usual way by hydrochloric acid titration and the formol titration method, which is a method of quantitatively analyzing for amino acid. As a result, the amounts of lithium ε-amino caproates produced were 96.5% and 96.8%, respectively, based on the amount of ε-caprolactam initially charged as a standard. On the other hand, the amount of carbon dioxide produced was 5.08 g (0.0479 mol) based on the amount of sodium carbonate as a standard, which, when converted to the production ratio of lithium ε-amino caproate, became 95.8%, a value well in accord with the aforementioned analyzed values.

The residue of the reaction liquid (the amount corresponding to 90% of the charged amount of lactam) was concentrated and distilled to obtain 13.5 g (purity: 98.3%) of white crystals of lithium ε-amino caproate. The production ratio of lithium ε-amino caproate based on the charged amount of lactam was 96.7%. Coarse crystals were recrystallized from a water-methanol solution, and purified lithium ε-amino caproate (melting point: 231°–233° C.) was obtained.

EXAMPLE 8

11.3 g (0.1 mol) of polycaproamide (nylon -6, $\eta_\gamma = 3.20$), 4.1 g (0.055 mol) of lithium carbonate and 90 ml of water were charged into the same autoclave as in Example 7. The temperature was elevated to 250° C., at which temperature the content of said autoclave was reacted for 6 hours. After completion of the reaction, the reaction liquid was treated by the same method as in Example 7 to obtain 13.7 g of lithium ε-amino caproate (purity: 98.6%, production ratio: 98.5%). The production ratio of lithium salt, calculated from the amount of carbon dioxide produced, was 99.2%.

EXAMPLE 9

11.3 g (0.1 mol) of oligocaproamide consisting mainly of the cyclic dimer and the cyclic trimer, 4.1 g (0.055 mol) of lithium carbonate and 90 ml of water were charged into the same autoclave as in Example 7. The temperature was elevated to 250° C., at which temperature the content of the autoclave was reacted in a nitrogen stream for 10 hours. After completion of the reaction, the reaction liquid was treated by the same method as in Example 7 to obtain 13.2 g of lithium ε-amino caproate (purity: 98.3%, production ratio: 95.0%). The production ratio of acid calculated from the amount of carbon dioxide produced was 95.3%.

What is claimed is:

1. In a process for preparing an amino Schiff base, from a starting material selected from the group consisting of ω-lactams having chain lengths of about 4–12 carbon atoms, oligomers thereof, ring-opened polymers thereof and ω-amino carboxylic acids corresponding thereto, the steps which comprise:

(a) heating said starting material with water and a carbonate of a metal selected from the group consisting of lithium, calcium and barium in a reaction container heated at a temperature of about 60°–350° C. and discharging carbon dioxide produced, thereby preparing a metal salt of an ω-amino carboxylic acid, (b) heating the resulting metal salt of said ω-amino carboxylic acid at a temperature of about 250°–550° C., thereby converting it to an amino Schiff base and/or a diamino ketone corresponding thereto, said Schiff base being represented by the following formula (I), and the diamino ketone being represented by the formula (II)

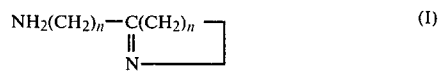

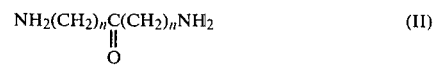

wherein n is an integer from 3–11, and also producing a carbonate compound of a metal selected from the group consisting of lithium, calcium and barium, and (c) recycling the metal carbonate compound produced in said heating step (b) to said heating step (a) for further use.

2. A process according to claim 1, wherein the number of carbon atoms is 4–6.

3. A process according to claim 2, wherein the number of carbon atoms is 6.

4. A process according to claim 1, wherein the metal is lithium.

5. A process according to claim 1, wherein the metal is calcium.

6. A process for preparing a metal salt of an ω-amino carboxylic acid, which process comprises heating a starting material consisting substantially of an ω-lactam having 4–12 carbon atoms, an oligomer thereof or a ring-opened polymer thereof, with water and a carbonate of a metal selected from the group consisting of lithium, calcium and barium in a reaction container heated at a temperature of about 60°–350° C., and discharging carbon dioxide produced.

7. A process for preparing an amino Schiff base and/or diamino ketone represented by the following formula (I) or (II):

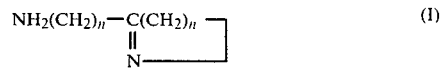

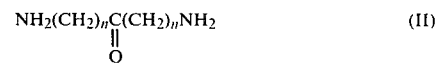

wherein n is an integer from 3–11,
and for also producing a carbonate of a metal selected from the group consisting of lithium, calcium and barium, which process comprises heating a metal salt of an ω-amino carboxylic acid having 4–12 carbon atoms, at a temperature of about 250°–550° C., for a time sufficient to dimerize the ω-amino carboxylic acid.

8. A process according to claim 6 or claim 7, wherein the number of carbon atoms is 4–6.

9. A process according to claim 6 or claim 7, wherein the number of carbon atoms is 6.

10. A process according to claim 6 or claim 7, wherein the metal is lithium.

11. A process according to claim 6 or claim 7, wherein the metal is calcium.

* * * * *

UNITED STATES PATENT AND TRADEMARK OFFICE
CERTIFICATE OF CORRECTION

PATENT NO. : 4,271,318
DATED : June 2, 1981
INVENTOR(S) : Tsutomu Setsuda, et al It is certified that error appears in the above-identified patent and that said Letters Patent are hereby corrected as shown below:

Table 4, column 7, delete "Lithium-2/3 aminoalkane" and insert --Lithium ω-aminoalkane.

Signed and Sealed this

Fifteenth Day of September 1981

[SEAL]

Attest:

Attesting Officer

GERALD J. MOSSINGHOFF

Commissioner of Patents and Trademarks